(12) United States Patent
Cripps et al.

(10) Patent No.: US 7,371,394 B2
(45) Date of Patent: May 13, 2008

(54) ANTIGENIC COMPOSITION OF A PSEUDOMONAS AERUGINOSA PROTEIN

(75) Inventors: Allan William Cripps, Canberra (AU); Jennelle Kyd, McKellar (AU); Margaret Dunkley, Elermore Vale (AU); Robert Llewellyn Clancy, Newcastle (AU)

(73) Assignee: Auspharm International Limited, Perth (AU)

( * ) Notice: Subject to any disclaimer, the term of this patent is extended or adjusted under 35 U.S.C. 154(b) by 510 days.

(21) Appl. No.: 11/158,599

(22) Filed: Jun. 22, 2005

(65) Prior Publication Data

US 2005/0232943 A1 Oct. 20, 2005

Related U.S. Application Data

(60) Division of application No. 09/359,426, filed on Jul. 22, 1999, now Pat. No. 7,029,684, which is a continuation-in-part of application No. PCT/GB98/00217, filed on Jan. 26, 1998.

(30) Foreign Application Priority Data

Jan. 24, 1997 (GB) ............................. 9701489.8

(51) Int. Cl.
*A61K 39/108* (2006.01)
*A61K 39/02* (2006.01)
*A61K 39/00* (2006.01)
*A61K 38/00* (2006.01)

(52) U.S. Cl. .............. 424/260.1; 424/234.1; 424/190.1; 424/184.1; 514/2

(58) Field of Classification Search ............ 424/260.1, 424/234.1, 184.1, 190.1; 514/2
See application file for complete search history.

(56) References Cited

U.S. PATENT DOCUMENTS

| 4,946,677 A | 8/1990 | Dorner et al. ............... 424/92 |
| 5,237,053 A | 8/1993 | Dorner et al. ............ 530/387.9 |

FOREIGN PATENT DOCUMENTS

| EP | 0252064 | 6/1987 |
| EP | 0717106 | 11/1995 |
| WO | 9006696 | 6/1990 |
| WO | 9324636 | 12/1993 |
| WO | 9741234 | 11/1997 |

OTHER PUBLICATIONS

Parkhill J et al., as published Oct. 15, 2001, "catalase [*Yersinia pestis*]" Genbank Accession No. NP_404811 GI:16121498.
Stover CK et al., as published Sep. 10, 2001, "catalase [*Pseudomonas aeruginosa*]" Genbank Accession No. NP_252926.1 GI:15599432.
Greenberg EP, 2000, "Bacterial genomics: pump up the versatility" *Nature* 406(6799):947-948.
Stover CK et al., 2000, "Complete genome sequence of *Pseudomonas aeruginosa* PA01, an opportunistic pathogen" *Nature* 406(6799):959-964.
Ma J et al., 1999, "Bacterioferritin A modulates catalase A (Kat A) activity and resistance to hydrogen peroxide in *Pseudomonas aeruginosa*" *Journal of Bacteriology* 181(12):3730-3742.
Nurizzo et al., 1997, Structure 5(9):1157-1171. N-terminal arm exchange is observed in the 2.15 A crystal structure of oxidized nitrite reductase from *Pseudomonas aeruginosa*.
Brown et al., 1995, J Bacteriol. 177(22):6536-44. Cloning and characterization of the katB gene of *Pseudomonas aeruginosa* encoding a hydrogen peroxide-inducible catalase: purification of KatB, cellular localization, and demonstration that it is essential for optimal resistance to hydrogen peroxide.
Yamano et al., 1994, Appl Microbiol Biotechnol 40:892-897. Ferric iron transport system of *Pseudomonas aeruginosa* PA01 that functions as the uptake pathway of a novel catechol-substituted cephalosporin, S-9096.
Sipos et al., 1991, Infect Immun. 59(9):3219-26. Cloning and sequencing of the genes coding for the 10- and 60-kDa heat shock proteins from *Pseudomonas aeruginosa* and mapping of a species-specific epitope.
Burgess et al., 1990, J Cell Biol. 111(5 Pt 1):2129-38. Possible dissociation of the heparin-binding and mitogenic activities of heparin-binding (acidic fibroblast) growth factor-1 from its receptor-binding activities by site-directed mutagenesis of a single lysine residue.
Meyer et al., 1990, Mol Microbiol. 1990 4(8):1401-5. Pyoverdin-facilitated iron uptake in *Pseudomonas aeruginosa*: immunological characterization of the ferripyoverdin receptor.
Yamano et al., 1990, J Antimicrob Chemother. 26(2):175-84. Outer membrane proteins responsible for the penetration of beta-lactams and quinolones in *Pseudomonas aeruginosa*.
Barbhaiya and Rao, 1988, FEMS Microbiology Letts 51:169-172. Iron uptake and detection of an outer membrane iron-siderophore receptor protein from *Pseudomonas aeruginosa* PA01.

(Continued)

*Primary Examiner*—S. Devi
(74) *Attorney, Agent, or Firm*—Baker Botts L.L.P.

(57) ABSTRACT

A novel antigen from *P. aeruginosa* is provided. The use of the antigen in detecting/diagnosing *P. aeruginosa* as well as its use in eliciting an immune response are also provided.

5 Claims, 1 Drawing Sheet

OTHER PUBLICATIONS

Kukor et al., 1988 J Bacteriol. 170(10):4458-65. Cloning and expression of the catA and catBC gene clusters from *Pseudomonas aeruginosa* PAO.

Lazar et al., 1988, Mol Cell Biol. 8(3):1247-52. Transforming growth factor alpha: mutation of aspartic acid 47 and leucine 48 results in different biological activities.

Yamaguchi et al., 1986, Japanese Journal of Bacteriology [Nippon Saikingaku Zasshi] 41(4):701-7. [Article in Japanese] The characterization of cross-reacting protein antigens in gram-negative bacilli.

Fernandes et al., 1981, Infect Immun. 33(2):527-32. Antibodies to cell envelope proteins of *Pseudomonas aeruginosa* in cystic fibrosis patients.

Sompolinsky et al., 1980 Acta Pathol Microbiol Scand [B]. 88(5):253-60An antigen common to a wide range of bacteria. 2. A biochemical study of a "common antigen" from *Pseudomonas aeruginosa*.

SEQUENCE LISTING

```
<160> NUMBER OF SEQ ID NOS: 2

<210> SEQ ID NO 1
<211> LENGTH: 19
<212> TYPE: PRT
<213> ORGANISM: P. Aeruginosa
<220> FEATURE:
<221> NAME/KEY: DOMAIN
<222> LOCATION: (1)...(19)
<223> OTHER INFORMATION: N-terminal sequence
<220> FEATURE:
<221> NAME/KEY: UNSURE
<222> LOCATION: 1
<223> OTHER INFORMATION: Possibly Ser
<220> FEATURE:
<221> NAME/KEY: UNSURE
<222> LOCATION: (5)...(6)
<223> OTHER INFORMATION: Probably Thr-Pro.  Possibly Ala-(Lys/Ser)
<220> FEATURE:
<221> NAME/KEY: UNSURE
<222> LOCATION: (8)...(14)
<223> OTHER INFORMATION: Probably Thr-Thr-Ala-Ala-Xaa-Ala-Pro.  Possibly
      Ala-(Ile/Asp)-Trp-(Phe/Leu)-(Gly/Ser)-Asn-Asp.
<220> FEATURE:
<221> NAME/KEY: UNSURE
<222> LOCATION: 17
<223> OTHER INFORMATION: Inconclusive sequencing data

<400> SEQUENCE: 1

Xaa Glu Glu Lys Xaa Xaa Leu Xaa Xaa Xaa Xaa Xaa Xaa Xaa Val Val
1               5                   10                  15

Xaa Asn Ala

<210> SEQ ID NO 2
<211> LENGTH: 19
<212> TYPE: PRT
<213> ORGANISM: P. Aeruginosa
<220> FEATURE:
<221> NAME/KEY: DOMAIN
<222> LOCATION: (1)...(19)
<223> OTHER INFORMATION: N-terminal sequence
<220> FEATURE:
<221> NAME/KEY: UNSURE
<222> LOCATION: 1
<223> OTHER INFORMATION: Possibly Ser
<220> FEATURE:
```

-continued

```
<221> NAME/KEY: UNSURE
<222> LOCATION: 12
<223> OTHER INFORMATION: Possibly Gly or Ser
<220> FEATURE:
<221> NAME/KEY: UNSURE
<222> LOCATION: 17
<223> OTHER INFORMATION: Inconclusive sequencing data

<400> SEQUENCE: 2

Xaa Glu Glu Lys Thr Pro Leu Thr Thr Ala Ala Xaa Ala Pro Val Val
 1               5                  10                  15

Xaa Asn Ala
```

ANTIGENIC COMPOSITION OF A PSEUDOMONAS AERUGINOSA PROTEIN

This application is a divisional of U.S. patent application Ser. No. 09/359,426 filed Jul. 22, 1999, now U.S. Pat. No. 7,029,684, which is a continuation-in-part of International Application Number PCT/GB98/00217, designating the United States, filed Jan. 26, 1998 and based on Great Britain Patent Application No. 9701489.8, filed Jan. 24, 1997, to each of which priority is claimed, and each of which is incorporated by reference in its entirety herein.

The present invention relates to a novel antigen from *Pseudomonas aeruginosa*, its use in medicine, particularly in the preparation of vaccines and in diagnosis.

BACKGROUND OF THE INVENTION

*P. aeruginosa* is a Gram-negative aerobic motile bacterium with the form of rods. It is an environmentally ubiquitous, extracellular, opportunistic pathogen that causes significant morbidity and mortality in compromised subjects. Infection is of particular significance in subjects with cystic fibrosis, burns, chronic bronchitis, bronchiectasis and cancer.

Identification of immune responses, the search for vaccine candidates and suitable components for diagnostic tests have focused on components of *P. aeruginosa*. The outer membrane of *P. aeruginosa* contains toxins, including the lipopolysaccharide endotoxin, phospholipid and proteins. The various outer membrane proteins (Opr) of *P. aeruginosa* have been assigned an alphabetical naming system. While several proteins have been characterised by this scheme, the expression of some is only transient and highly dependent upon nutrient availability, culture conditions and the presence of antibiotics. Presently, three major Oprs, designated F,H2 and I, are recognised as antigenically common to and expressed in high copy numbers in all strains of *P. aeruginosa*.

DETAILED DESCRIPTION OF THE INVENTION

Figure 1:
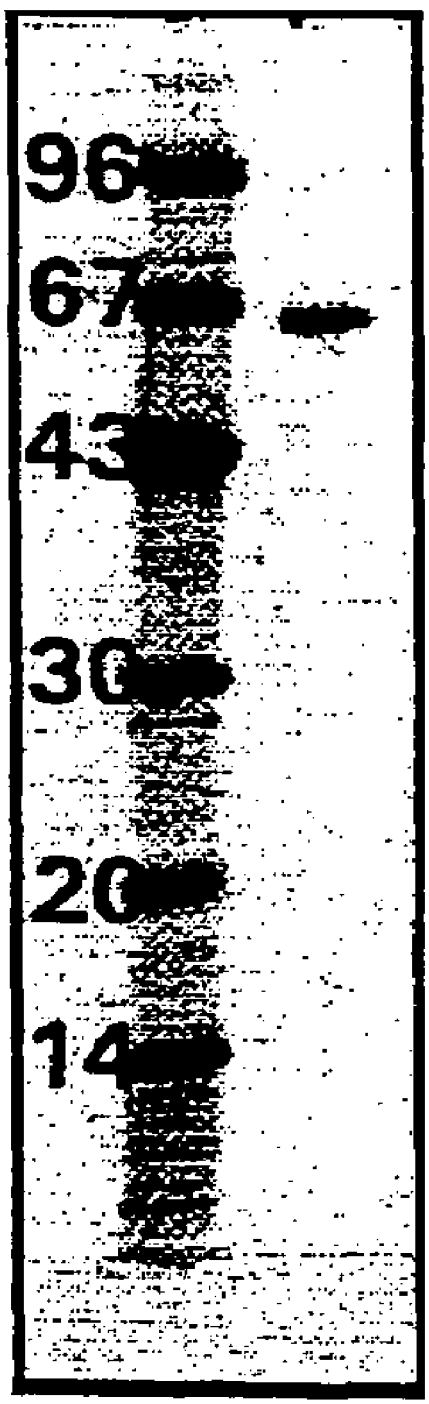
FIG. 1 depicts the separation of a protein preparation from *P. aeruginosa* by SDS-PAGE, and the position of Pa60 as visualized by protein staining.

We have now identified a protein from an outer membrane preparation of *P. aeruginosa*, which we have designated Pa60. The amino-terminal sequence of this protein does not demonstrate any sequence homology with other previously characterised proteins (GenBank data search). This protein is antigenic and is capable of inducing a protective immune response resulting in enhanced clearance of *P. aeruginosa*.

Thus, in a first aspect the present invention provides a protein antigen from *P. aeruginosa* and having a molecular weight in the range of about 60 kDa to about 65 kDa, as determined by SDS-PAGE.

In a preferred embodiment the protein has the following N-terminal sequence:
Xaa-E-E-K-Xaa-Xaa-L-Xaa-Xaa-Xaa-Xaa-Xaa-Xaa-V-V-Xaa-N-A (SEQ ID NO:1); and preferably:
Xaa-E-E-K-T-P-L-T-T-A-A-Xaa-A-P-V-V-Xaa-N-A (SEQ ID NO:2).

Parts or fragments of the whole protein may themselves be antigenic and thus, in a second aspect, the present invention provides an antigenic fragment of the protein of the invention. In particular, the antigenic fragment will comprise the N-terminal sequence as described above.

The skilled man will appreciate that some variation in the sequence of fragments will be possible, while still retaining antigenic properties. Methods well known to the skilled man can be used to test fragments and/or variants thereof for antigenicity. Such variants also form part of the invention.

The antigenic protein, or fragments thereof, of the present invention can be provided alone, as a purified or isolated preparation, or as part of a mixture with other *P. aeruginosa* antigenic proteins.

In a third aspect, therefore, the invention provides an antigen composition comprising one or more proteins of the invention and/or one or more antigenic fragments thereof. Such a composition can be used for the detection and/or diagnosis of *P. aeruginosa*. In one embodiment the composition comprises one or more additional *P. aeruginosa* antigens.

In a fourth aspect, the present invention provides a method of detecting and/or diagnosing *P. aeruginosa* which comprises:
 (a) bringing into contact an antigenic protein, or antigenic fragment thereof, or an antigen composition of the invention with a sample to be tested; and
 (b) detecting the presence of antibodies to *P. aeruginosa*.

In particular, the proteins, antigenic fragment thereof or antigen composition of the invention can be used to detect IgG antibodies. Suitably, the sample to be tested will be a biological sample, e.g. a sample of blood or saliva.

In a fifth aspect, the invention provides the use of an antigenic protein, antigenic fragment thereof or antigenic composition of the present invention in detecting and/or diagnosing *P. aeruginosa*. Preferably, the detecting and/or diagnosing is carried out in vitro.

The antigenic protein, antigenic fragment thereof or antigen composition of the invention can be provided as part of a kit for use in in vitro detection and/or diagnosis of *P. aeruginosa*. Thus, in a sixth aspect, the present invention provides a kit for use in the detection and/or diagnosis of *P. aeruginosa* comprising an antigenic protein, antigenic fragment thereof or antigen composition of the invention.

In addition, the antigenic protein or antigenic fragment thereof of the invention can be used to induce an immune response against *P. aeruginosa*. Thus, in a further aspect, the present invention provides the use of an antigen of the invention, a fragment thereof or an antigenic composition of the invention in medicine.

In yet a further aspect the present invention provides a composition capable of eliciting an immune response in a subject which comprises a protein or one or more antigenic fragments thereof of the invention. Suitably, the composition will be a vaccine composition, optionally comprising one or other suitable adjuvants. Such a vaccine composition may be either a prophylactic or therapeutic vaccine composition.

The vaccine compositions of the invention can include one or more adjuvants. Examples of adjuvants well known in the art include inorganic gels such as aluminium hydroxide or water-in-oil emulsions such as incomplete Freund's adjuvant. Other useful adjuvants will be well known to the skilled man.

In yet further aspects, the present invention provides:
(a) the use of a protein or one or more antigenic fragments thereof of the invention in the preparation of an immunogenic composition, preferably a vaccine;
(b) the use of such an immunogenic composition in inducing an immune response in a subject; and
(c) a method for the treatment or prophylaxis of *P. aeruginosa* infection in a subject, which comprises the step of administering to the subject an effective amount of a protein, at least one antigenic fragment or an antigen composition of the invention, preferably as a vaccine.

Preferred features of each aspect of the invention are as for each other aspect mutatis mutandis.

The invention will now be described with reference to the following example which should not be construed as limiting the invention in any way.

The examples refer to the FIGURE in which:
FIG. 1: shows SDS-PAGE analysis of Pa60.

EXAMPLE 1

Protein Purification

*Pseudomonas aeruginosa* bacteria, strain 385 (Pa385), were harvested from overnight culture of 100 agar plates by scraping the plates followed by washing twice by centrifugation at 10,000×g for 10 minutes at 4° C. A crude outer membrane preparation was obtained by extraction of the outer membrane component with buffered ZWITTERGENT 3-14 detergent and ethanol precipitation.

The outer membrane extract was lyophilised and resuspended in starting buffer (20 mM Tris, pH8.5). This preparation was subjected to anion exchange chromatography using a Q2 column (BioRad) and a sodium chloride gradient to elute the proteins. The fractions eluted from the column were initially assessed for protein content by analytical SDS-PAGE. From this was determined the elution of profile for Pa60 allowing fractions containing Pa60 to be collected from susequent runs for further purification. These fractions were dialysed against distilled water, lyophilised, resuspended in a minimal amount of distilled water and further dissolved in 4 times the volume of sodium dodecyl sulphate (SDS) reducing buffer (62.5 mM Tris, pH6.8, 10% (v/v) glycerol, 2% (w/v) SDS, 5% (v/v) B-mercaptoethanol, 1.2× $10^{-3}$% (w/v) bromophenol blue). The SDS preparation was incubated at 37° C. for at least 30 min prior to being loaded onto the stacking gel of the electrophoresis column.

Pa60 was purified using preparative polyacrylamide electrophoresis (PAGE). Preparative SDS-PAGE was performed using the BioRad model 491 PREP CELL (a continuous elution electrophoresis apparatus) using a 9% T-1.42% C acrylamide/BIS (N,N'-methylene-bisacrylamide) separating gel with a 10 ml 4% T-0.36% C acrylamide/BIS stacking gel polymerized in a 28 mm (internal diameter) column. Fractions eluted from the column were concentrated by lyophilization and analyzed for protein content by analytical SDS-PAGE. Pa60 isolated using these conditions contained SDS which was subsequently removed by potassium phosphate precipitation. Fractions containing Pa60 were pooled and dialyzed prior to determination of protein concentration.

Analytical identification of the protein was performed by analytical SDS-PAGE using either gradient 10-15% or homogenous 12.5% acrylamide gels and coomassie or silver stained. Protein concentration was determined using the Pierce micro BCA assay.

Results

Pa60 was successfully separated from other *P. aeruginosa* proteins by the described method. FIG. 1 shows the position of this protein on SDS-PAGE.

EXAMPLE 2

N-Terminal Sequencing of Pa60

Pa60 was prepared for N-terminal amino acid analysis by excising the region containing the protein from an SDS-PAGE gel. The gel segments were sent to both the Biomolecular resouirce facility, Australian National University, Canberra, Australia and MUCAB Services, Macquarie University, North ryde, NSW, Australia.

Results

An N-terminal amino acid sequence was obtained which identified sixteen of the first nineteen amino acids. Possible amino acids were identified for the remaining residues and where there was uncertainty with a probable identification.

| SEQUENCE: | | | | | | | | | |
|---|---|---|---|---|---|---|---|---|---|
| | 1 | 2 | 3 | 4 | 5 | 6 | 7 | 8 | 9 | 10 |
| Definite | | E | E | K | | | L | | | |
| Probable | | | | | T | P | | T | T | A |
| Possible | S | | | | A | L/S | | A | I/D | W |

| | 11 | 12 | 13 | 14 | 15 | 16 | 17 | 18 | 19 |
|---|---|---|---|---|---|---|---|---|---|
| Definite | | | | | V | V | | N | A |
| Probable | A | | A | P | | | | | |
| Possible | F/L | G/S | N | D | | | | | |

This provides a sequence with the following definite amino acids:

```
1 - 2-3-4-5 - 6  -7-8 - 9 - 10 -11- 12- 13 -14-15-16-17-18-19

Xaa-E-E-K-Xaa-Xaa-L-Xaa-Xaa-Xaa-Xaa-Xaa-Xaa-Xaa-V- V-Xaa-N -A   (SEQ ID NO:1)
```

If one includes probable amino acids the following sequence is obtained:

```
1 - 2-3-4-5-6-7-8-9-10-11-12-13-14-15-16-17-18-19

Xaa-E-E-K-T-P-L-T-T -A -A-Xaa-A -P -V -V-Xaa-N -A (SEQ ID NO:2)
```

EXAMPLE 3

Bacterial Clearance Following Immunisation in a Rat Model

Specific pathogen free male rats received an intra-Peyer's patch (IPP) immunisation on day 1 and the live bacterial challenge on day 14. The animals were sedated by anaesthesia. The small intestine was exposed through a mid-line abdominal incision and the antigen injected subserosal to each Peyer's patch using a 27-gauge needle. The immunisation protein (Pa60) was prepared by emulsification of 200 or 800 μg of protein per ml in a 1:1 ratio of Incomplete Freund's adjuvant (IFA) and phosphate buffered saline (PBS) and a total inoculum of 10 or 40 μg of protein respectively was administered to each animal. Animals were challenged for 4 hours with live bacteria (bacteria count $5 \times 10^8$ CFU) 14 days after the immunisation. Bacteria were grown overnight at 37° C. in 5% $CO_2$ on nutrient agar plates, recovered, washed and resuspended in PBS to the required concentration. Bacteria were introduced into the lungs via an intra-tracheal cannula and 4 hours later the rats were euthanased. Blood was collected and aliquots of serum stored at −20° C. for antibody analysis. Lungs were lavaged by flushing with 5×2 ml of PBS and the pooled lavage (BAL) assessed for bacteria numbers. Following lung lavage, the lungs were removed, homogenised and assessed for numbers of bacteria. Cytospin slides were prepared for determination of differential cell counts in the lung lavage. total cell numbers present in the lung lavage were calculated by staining with trypan blue and counting using a haemocytometer.

Results

Rats immunised with Pa60 and challenged with live bacteria of the Pa385 homologous strain on day 14 showed an enhancement of bacterial clearance. Rats immunised with both 10 μg or 40 μg Pa60 had fewer bacteria recovered in both the BAL and lung than the non-immune group after 4 hours (Table 1).

Greater numbers of phagocytic cells were present in the BAL of Pa60-immunised animals and correlated with the enhanced bacterial clearance in these animals (table 2).

TABLE 1

Pulmonary clearance following Pa60 immunisation and challenge with *P. aeruginosa* (strain 385)

| | | *P. aeruginosa* recovered 4 h post-challenge ($\log_{10}$CFU)[a] | |
|---|---|---|---|
| RAT GROUP | n[b] | BAL | LUNG HOMOG. |
| NON-IMMUNE | 5 | 7.63 ± 0.11 | 8.66 ± 0.18 |
| 10 μg Pa60 | 6 | 6.95 ± 0.07 | 8.43 ± 0.09 |
| 40 μg Pa60 | 4 | 7.19 ± 0.07 | 8.37 ± 0.19 |

TABLE 2

Cell count of Phagocytes in BAL following bacterial challenge

| ANIMAL GROUP | TOTAL PHAGOCYTIC CELLS IN BAL |
|---|---|
| NON-IMMUNE | 1.2 (±0.3) × $10^6$ |
| 10 μg Pa60 | 4.3 (±1.2) × $10^6$ |
| 40 μg Pa60 | 7.4 (±1.7) × $10^6$ |

EXAMPLE 4

Clinical Diagnostic Study

Children from the Royal Children's Hospital in Melbourne that had been diagnosed with cystic fibrosis provided samples for this study. Bronchoalveolar lavage (BAL) abnd serum were collected over a 3-4 year period from patients from the time of diagnosis as an infant. The samples were divided into groups based on clinical status of *P. aeruginosa*.

Group 1: Non-cystic fibrosis controls (age matched children with Stridor);

Group 2: Negative for *P. aeruginosa*;

Group 3: Upper respiratory tract isolation of *P. aeruginosa*, negative *P. aeruginosa* in lower respiratory tract;

Group 4: Cleared *P. aeruginosa* in the lower respiratory tract (negative in the next BAL sample); and Group 5: Positive for *P. aeruginosa* in consecutive BAL samples.

An enzyme linked immunosorbent assay (ELISA) was used to measure antibodies to Pa60 in BAL and serum samples. Polysorb microtiter wells were coated with purified Pa60 at a concentration of 1 µg per ml (one microgram per milliliter). The plates were washed five times in phosphate buffered saline (PBS) containing 0.05% TWEEN 20 (a surfactant and spreading agent that is also known generically as Polysorbate 20) between incubation steps. The wells were blocked with skim milk in PBS-0.05% TWEEN 20 for 60 minutes. Wells were incubated for 90 minutes with serum or BAL samples that were diluted in blocking buffer for analysis. Conjugated immunoglobulins used were rabbit anti-human IgG, IgA and IgM and wells were incubated with conjugated immunoglobulins for 90 minutes. The plates were then developed. Human IgG, IgA and IgM were used to quantitate the antibody.

Results

An increase in antibody titre was observed as the incidence of infection with *P. aeruginosa* occurred. The non-cystic fibrosis control group and the non-infected cystic fibrosis patients had negligible titresto Pa60. Increased titres of IgG to Pa60 were observed, particularly in the patients with consecutive *P. aeruginosa* culture from the BAL (Group 5). In the BAL a significant increase in IgA titre was observed.

TABLE 3

Pa60-specific Antibody in Serum and Bronchoalveolar lavage from cystic fibrosis and non-cystic fibrosis children

| PATIENTS | SERUM[a] | | | BAL[a] | | |
|---|---|---|---|---|---|---|
| | IgG | IgA | IgM | IgG | IgA | IgM |
| GROUP 1 | 1.74 | 0.11 | 0.67 | 0.03 | 0.05 | 0.02 |
| GROUP 2 | 1.40 | 2.34 | 2.10 | 0.03 | 0 | 0.02 |
| GROUP 3 | 7.08 ± 8.4 | 10.9 ± 18 | 2.03 ± 2.5 | 0.03 ± 0.01 | 0.21 ± 0.13 | 0.03 ± 0.01 |
| GROUP 4 | 18.9 ± 21.9 | 0.56 ± 0.6 | 1.46 ± 2.07 | 0.02 ± 0.01 | 0.12 ± 0.04 | 0.01 ± 0.01 |
| GROUP 5 | 54.5 ± 76 | 7.5 ± 12.5 | 6.2 ± 0.5 | 0.03 ± 0.01 | 0.81 ± 0.30 | 0.03 ± 0.01 |

EXAMPLE 5

Pulmonary Challenge of rats with *Pseudomonas aeruginosa* following mucosal immunisation with Pa60.

DA rats were immunised with Pa60 such that they received 10 µg Pa60 administered to intestinal Peyer's Patches (IPP). The Pa60 was delivered emulsified in Incomplete Freund's adjuvant. Fourteen days post-IPP, all the immunised rats received an intra tracheal (IT) boost with 10 µg Pa60 in phosphate buffered saline. Seven days post-IT boost, the immunised group and an untreated control group were challenged via IT administered of $5 \times 10^8$ CFU live *P. aeruginosa*. The rats were killed and samples collected for analysis at 4 h post-challenge.

Results

Bacterial Clearance

Bacterial recovery in bronchoalveolar lavage (BAL) and lung tissue

| Bacterial Recovery ($\log_{10}$ CFU)* | | | |
|---|---|---|---|
| Group | n+ | BAL | Lung |
| Non-immune | 5 | 7.92 ± 0.11 | 9.01 ± 0.15 |
| 10 µg Pa60 | 5 | 6.34 ± 0.08 | 7.58 ± 0.08 |

*Data expressed as mean ± S.E.M.
+number of animals

Rats immunised IPP with an IT boost at day 14 significantly cleared the *P. aeruginosa* from both the BAL and lung tissue.

White Cell Recruitment to Infection

White Cell Count in BAL

| Group | n | White cell count* ×10$^6$ |
|---|---|---|
| non-immune | 5 | 6.8 ± 1.4 |
| 10 µg Pa60 | 5 | 36.0 ± 5.0 |

*data represents mean ± S.E.M.

Rats immunised with Pa60 more rapidly recruited white cells to the lungs following bacterial challenge. Nearly all the white cells recovered in the BAL were either polymorphonuclear neutrophils (PMNs) or macrophages. The early recruitment of white cells to the bronchoalveolar spaces correlated with bacterial clearance.

Antibody Responses

Antibody in serum and BAL following mucosal immunisation with Pa60

| Antibody in Serum | | | | |
|---|---|---|---|---|
| Group | n | IgG* | IgA* | IgM* |
| non-immune | 5 | 0 | 0 | 14.8 ± 0.56 |
| 10 µg Pa60 | 5 | 1310 ± 119 | 10 ± 2 | 100 ± 59 |

*IgG, IgA and IgM expressed as Elisa units

Serum antibody to Pa60 was detected in immunised rats. There were significant titers of IgG, IgA and IgM.

Antibody in BAL

| Group | n | IgG* | IgA* | IgM* |
|---|---|---|---|---|
| non-immune | 5 | 1.5 ± 0.2 | 0 | 0.5 ± 0.02 |
| 10 μg Pa60 | 5 | 21.3 ± 2.6 | 7.8 ± 4.2 | 0.8 ± 0.3 |

*IgG, IgA and IgM expressed as Elisa units

Antibody to Pa60 was detected in the BAL in immunised animals. There were significant titers of both IgG and IgA specific for Pa60.

In a particular embodiment, this invention provides a kit for detection or diagnosis of *P. aeruginosa* in a sample from a patient. The kit contains at least one or more antigens or antigenic fragments according to this invention, along with the means to detect binding between the antigens or fragments and antibodies which specifically bind such antigens or fragments. Selection of suitable means for detecting antigen-antibody binding is easily within the skill of the ordinary worker in this art, and include primary and/or secondary labeled antibodies to IgG from humans or other mammals, and/or other known materials for sandwich assays, ELISA assays, competitive immunoassays, and other well known immunometric assay formats.

In yet another particular embodiment, this invention provides a method for diagnosing *P. aeruginosa* in a subject suffering from cystic fibrosis. This method comprises bringing into contact one of the proteins, antigenic fragments or antigen compositions disclosed in this invention with a biological sample obtained from a subject with cystic fibrosis. The biological sample is preferably a sample of mucous, e.g., saliva. This method further comprises detecting the presence of antibodies to *P. aeruginosa* in such a sample by, for example, detecting binding between the antigens or fragments and antibodies which specifically bind such antigens or fragments, using detection means which are of common knowledge to those of skill in the art.

The invention claimed is:

1. A method of eliciting an immune response in a subject against *Pseudomonas aeruginosa* infection comprising administering to said subject an amount of an immunogenic composition comprising an isolated *Pseudomonas aeruginosa* protein having a molecular weight of about 60 kDa to about 65 kDa and an N-terminal sequence comprising the amino acid sequence of SEQ ID NO: 2, or an isolated antigenic fragment of said protein, wherein said antigenic fragment comprises at its N-terminus the amino acid sequence of SEQ ID NO: 2.

2. The method of claim 1, wherein the immunogenic composition further comprises one or more adjuvants.

3. The method of claim 1, wherein the immunogenic composition further comprises a pharmaceutically acceptable carrier.

4. The method of claim 1, wherein the immunogenic composition further comprises one or more additional *Pseudomonas aeruginosa* antigens.

5. The method of claim 1, wherein the immunogenic composition is a vaccine composition.

* * * * *